US00PP21274P3

(12) United States Plant Patent
Meinl

(10) Patent No.: US PP21,274 P3
(45) Date of Patent: Sep. 7, 2010

(54) **VARIETY OF *HYDRANGEA* PLANT NAMED 'HORSTOL'**

(50) Latin Name: ***Hydrangea macrophylla* hybrid**
Varietal Denomination: Horstol

(75) Inventor: Katrin Meinl, Dresden (DE)

(73) Assignee: Claus & Torsten Kühne GbR, Dresden (DE)

( * ) Notice: Subject to any disclaimer, the term of this patent is extended or adjusted under 35 U.S.C. 154(b) by 0 days.

(21) Appl. No.: 12/313,825

(22) Filed: Nov. 25, 2008

(65) Prior Publication Data

US 2010/0132084 P1 May 27, 2010

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant Variety Database 2009/03 p. 1.*

* cited by examiner

*Primary Examiner*—Annette H Para
(74) *Attorney, Agent, or Firm*—The Webb Law Firm

(57) ABSTRACT

A new and distinct *Hydrangea* plant having a strong root system, good stem quality and deep pink colored inflorescences.

1 Drawing Sheet

Botanical classification: *Hydrangea macrophylla* hybrid.
Varietal denomination: 'Horstol'.

BACKGROUND OF THE INVENTION

The present invention comprises a new and distinct cultivar of *Hydrangea* plant known by the varietal name 'Horstol'. The new variety was discovered in 2001 in a planned breeding program in Dresden, Germany. The purpose of the breeding program was to develop vigorous dark pink/red *Hydrangeas*. The new variety is the result of a cross between breeding selection 48-90/1 (female parent, unpatented) and 'Rom' (male parent, unpatented). The color of 'Horstol' is similar to 48-90/1, but 'Horstol' differs in growth habit and inflorescence diameter. The forcing time of 'Horstol' is similar to 'Rom', but 'Horstol' differs in color and growth habit. The new variety was first asexually reproduced in 2001 via propagation by cuttings in Germany. The new variety has been trial and field tested in Germany and has been found to retain its distinctive characteristics and remain true to type through successive propagations.

The following traits distinguish 'Horstol' as a new and distinct cultivar from other *Hydrangea* varieties known to the breeder:

1. Inflorescence size;
2. Stem quality;
3. Vigor;
4. Root system; and
5. Branching characteristics.

'Horstol' is similar to another *Hydrangea* variety, 'Merrits Supreme' (unpatented), in color and because they are both mopheads. However, 'Horstol' differs from 'Merrits Supreme' in growth habit, branching characteristics and forcing time.

DESCRIPTION OF THE DRAWING

The accompanying photographic drawing illustrates the new variety, with the color being as nearly true as is possible with color illustrations of this type.

DESCRIPTION OF THE PLANT

Figure 1:
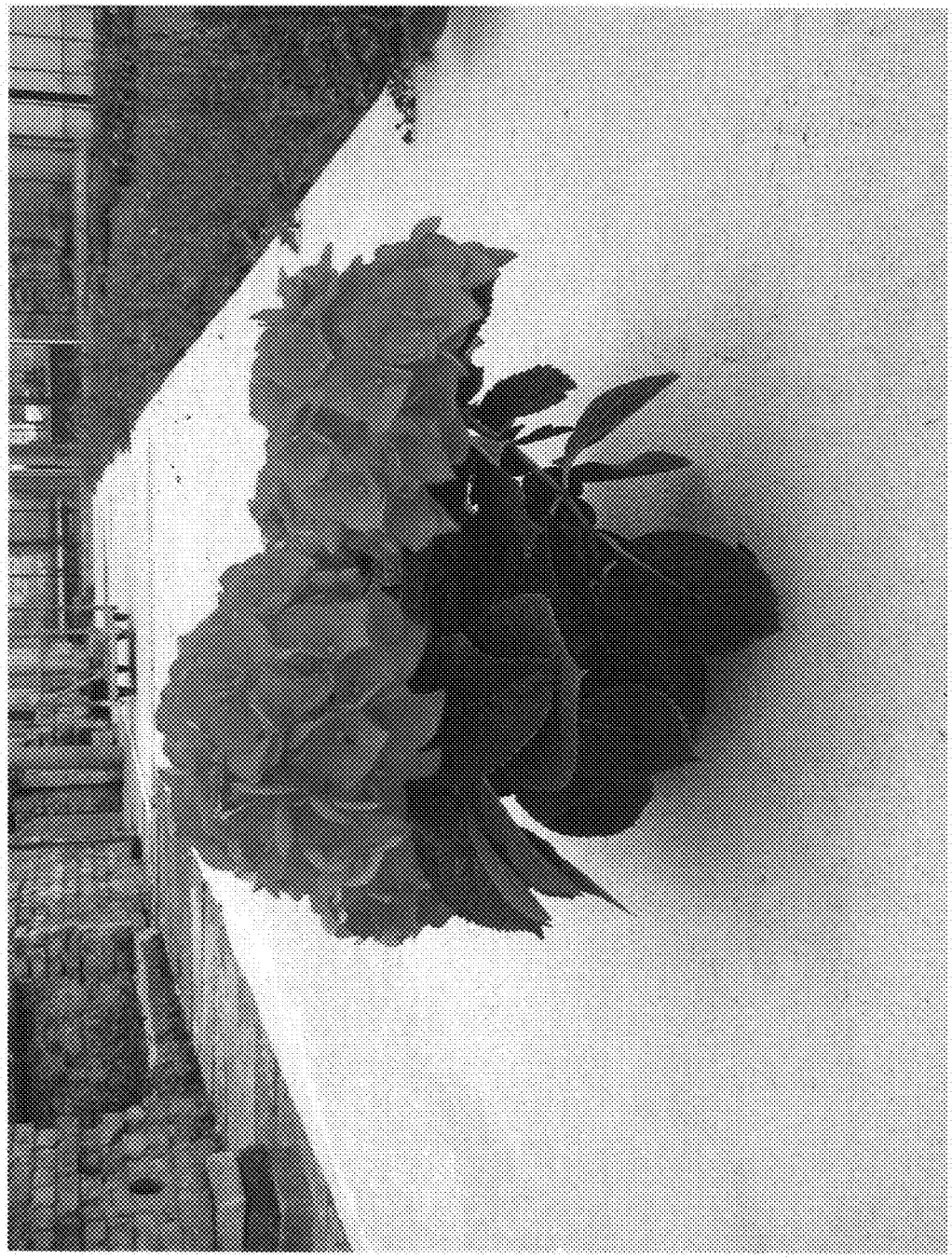
FIG. 1 is photograph of an entire plant of the new variety.

The following detailed description sets forth characteristics of the new cultivar. The plants were grown in 13 cm. pots in peat substrate at a pH of 5.7 and were 10 months past propagation when described. Measurements and color readings of the plants were taken in Dresden, Germany under natural light with a shadow present. Color references are primarily to the R.H.S. Colour Chart of The Royal Horticultural Society of London.

PLANT

Time to initiate roots: About 15 days at 18° C.
Time to develop roots: About 20 days at 18° C.
Rooting habit: Strong and adventitious root system.
Time to produce a finished flowering plant from a rooted cutting: About 43 weeks in a 13 cm. container.
Form: Symmetrical.
Height (from media surface to top of foliage): 20.0 cm.
Height (from media surface to top of flowers): 29.0 cm.
Plant diameter: 45.0 cm.
Vigor: Strong.
Strength: No artificial support needed.
Branching habit: Well-branched.
Trunk:
- *Main trunk length.*—0.8 cm.
- *Diameter.*—0.8 cm.
- *Color.*—199B.
- *Texture.*—Woody.
- *Pubescence.*—Absent.
- *Internode length.*—1.2 cm.

Lateral branches:
- *Length.*—Young: 14.0 cm. Mature: 2.0 cm.
- *Diameter.*—Young: 0.7 cm. Mature: 0.9 cm.
- *Internode length*—2.0 cm.
- *Texture.*—Smooth with dark lenticels.
- *Pubescence.*—Absent.

*Lenticel.*—Length.—0.5-1.0 mm. Width: 0.5 mm. Shape: Mostly oval.
*Color.*—Young: 144A. Mature: 199B.
*Lenticel color.*—177A.

Foliage:
*Arrangement.*—Mostly opposite disposition.
*Size of leaf.*—Length: 10.0 cm. Width: 7.0 cm.
*Shape of leaf* (*generally*).—Young: Ovate. Mature: Ovate.
*Shape of apex.*—Cuspidate.
*Shape of base.*—Obtuse.
*Texture.*—Shiny.
*Aspect.*—Slightly undulate.
*Margin type.*—Serrate.
*Pubescence.*—None present.
*Color.*—Young leaves: Upper surface: 139A. Lower surface: 138B. Mature leaves: Upper surface: 139A. Lower surface: 138B.
*Petiole.*—Shape: U-shaped. Length: 1.8 cm. Diameter: 0.3 cm. Color: 138B.
*Veins.*—Venation type: Pinnate. Color: Upper surface: 138B. Lower surface: 138C.

FLOWER

Natural flowering season: July in Dresden, Germany.
Flower habit: Late blooming after 10 weeks of forcing.

Bud:
*Stage of development when described.*—At full coloration.
*Shape of cluster.*—Round.
*Diameter of cluster.*—6.0 cm.
*Number of buds per cluster.*—5 fertile, 15 sterile.
*Shape.*—Fertile: Round. Sterile: Round.
*Length.*—Fertile: 0.4 cm. Sterile: 0.2 cm.
*Width.*—Fertile: 0.4 cm. Sterile: 0.2 cm.

Inflorescence:
*Shape.*—Mophead.
*Length.*—10.0 cm.
*Diameter.*—15.0 cm.
*Average number of flowers per inflorescence.*—30 fertile, 85 sterile.
*Average number of inflorescences per plant.*—6.
*Lastingness.*—Fertile: Three weeks. Sterile: Five weeks.

Petals:
*Number per flower:* 4 to 6.
*Color.*—Upper surface: 63B. Lower surface: 63D.
*Shape.*—Round to ovate.
*Length.*—0.4 cm.
*Width.*—0.2 cm.
*Apex.*—Pointy.
*Base.*—Obtuse.
*Margin.*—Entire.
*Texture.*—Smooth.
*Tonality from a distance.*—Mixed color.

Sepals:
*Number per flower.*—4 to 5.
*Color.*—142D.
*Shape.*—Ovate.
*Length*—0.1 cm.
*Width.*—0.1 cm.
*Apex.*—Pointy.
*Base.*—Obtuse.
*Margin.*—Entire.
*Texture.*—Smooth.
*Fused.*—Yes.

Petaloids:
*Quantity.*—4 to 5.
*Shape.*—Ovate.
*Length.*—2.8 cm.
*Width.*—2.8 cm.
*Color.*—Upper surface: N66B. Lower surface: 68B.

Pedicels:
*Length.*—Fertile: 0.4 cm. Sterile: 2.8 cm.
*Diameter.*—Fertile: 0.1 cm. Sterile: 0.2 cm.
*Color.*—68C.

Peduncles:
*Length.*—4.0 cm.
*Diameter.*—0.4 cm.
*Texture.*—Smooth with dark lenticels.
*Color.*—144C.

Stamens:
*Number per fertile flower.*—7 to 9.
*Filament.* Length: 0.2 cm. Color: 65D.
*Anthers.*—Shape: Round to elongated. Length: 0.1 cm. Color: 1D.
*Pollen.*—Color: 1D. Amount: Plentiful.

Pistils:
*Number.*—1, divided into 3 parts.
*Length.*—0.1 cm.
*Style: Length:* 0.1 cm. Color: 65D.
*Stigma* (*divided into* 3 *parts*).—Color: 65D. Diameter: 0.2 cm.
*Ovaries* (*inferior*).—Length: 0.3 cm. Width: 0.2 cm. Color: 1D.

Fragrance: Fresh and "green".
Disease resistance: Tolerant to botrytis and powdery mildew.
Temperature tolerance: Medium, not fully winterhardy flower buds in Germany.
Drought tolerance: Medium.

I claim:

1. A new and distinct variety of *Hydrangea* plant substantially as shown and described herein.

* * * * *